United States Patent
Satou et al.

(10) Patent No.: US 12,394,244 B2
(45) Date of Patent: *Aug. 19, 2025

(54) BIOLOGICAL PATTERN INFORMATION PROCESSING DEVICE, BIOLOGICAL PATTERN INFORMATION PROCESSING METHOD, AND PROGRAM

(71) Applicant: NEC Corporation, Tokyo (JP)

(72) Inventors: Kan Satou, Tokyo (JP); Yoshinori Suzuki, Tokyo (JP); Masanori Mizoguchi, Tokyo (JP); Masanori Hara, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/809,541

(22) Filed: Aug. 20, 2024

(65) Prior Publication Data

US 2024/0412555 A1  Dec. 12, 2024

Related U.S. Application Data

(63) Continuation of application No. 18/078,232, filed on Dec. 9, 2022, now Pat. No. 12,190,630, which is a (Continued)

(30) Foreign Application Priority Data

Mar. 31, 2015 (JP) .................................. 2015-074479

(51) Int. Cl.
*G06V 40/12* (2022.01)

(52) U.S. Cl.
CPC ...... *G06V 40/1376* (2022.01); *G06V 40/1359* (2022.01)

(58) Field of Classification Search
CPC ............................................ G06V 40/12–1394
See application file for complete search history.

(56) References Cited

U.S. PATENT DOCUMENTS

| | | | | |
|---|---|---|---|---|
| 5,519,785 A | * | 5/1996 | Hara | G06V 40/1347 382/311 |
| 5,659,626 A | | 8/1997 | Ort | |

(Continued)

FOREIGN PATENT DOCUMENTS

| | | |
|---|---|---|
| JP | 9-44666 A | 2/1997 |
| JP | 10-167266 A | 7/1998 |

(Continued)

OTHER PUBLICATIONS

Asker Bazen, "Fingerprint Identification: Feature Extraction, Matching, and Database Search", Twente University, Aug. 19, 2002.

(Continued)

*Primary Examiner* — Patrick F Marinelli
(74) *Attorney, Agent, or Firm* — Sughrue Mion, PLLC

(57) ABSTRACT

A biological pattern information processing device includes: a biological pattern information acquisition unit that acquires biological pattern information indicating a biological pattern; and a singular region detection unit that detects a singular region including damage, from the biological pattern indicated by the acquired biological pattern information.

11 Claims, 12 Drawing Sheets

Related U.S. Application Data continuation of application No. 17/364,164, filed on Jun. 30, 2021, now Pat. No. 11,557,146, which is a continuation of application No. 15/563,211, filed as application No. PCT/JP2016/060336 on Mar. 30, 2016, now Pat. No. 11,055,511.

(56) References Cited

U.S. PATENT DOCUMENTS

| | | | |
|---|---|---|---|
| 5,848,176 A * | 12/1998 | Hara | G06V 40/1347 |
| | | | 382/125 |
| 5,937,082 A * | 8/1999 | Funada | G06V 40/1347 |
| | | | 382/125 |
| 6,049,621 A | 4/2000 | Jain | |
| 8,876,299 B2 * | 11/2014 | Song | F16M 11/10 |
| | | | 353/70 |
| 9,418,276 B2 * | 8/2016 | Yamada | G06V 40/1376 |
| 10,628,657 B2 * | 4/2020 | Mizoguchi | G06V 40/1388 |
| 10,853,620 B2 * | 12/2020 | Mizoguchi | G06F 21/32 |
| 10,853,621 B2 * | 12/2020 | Mizoguchi | G06V 40/1394 |
| 10,867,160 B2 * | 12/2020 | Mizoguchi | G06V 40/1394 |
| 10,915,728 B2 * | 2/2021 | Norimatsu | G06V 40/1376 |
| 11,055,511 B2 * | 7/2021 | Satou | A61B 5/117 |
| 11,557,146 B2 * | 1/2023 | Satou | G06V 40/1359 |
| 11,776,304 B2 * | 10/2023 | Norimatsu | G06V 40/1376 |
| | | | 382/125 |
| 2001/0036297 A1 | 11/2001 | Ikegami | |
| 2002/0164056 A1 * | 11/2002 | Funada | G06V 40/1347 |
| | | | 382/124 |
| 2003/0021452 A1 * | 1/2003 | Hamid | G06V 40/1347 |
| | | | 382/124 |
| 2003/0076986 A1 | 4/2003 | Yoon | |
| 2012/0189171 A1 | 7/2012 | Abiko | |
| 2012/0195475 A1 | 8/2012 | Abiko | |
| 2012/0224041 A1 * | 9/2012 | Monden | G06V 10/26 |
| | | | 348/E7.085 |
| 2013/0216095 A1 | 8/2013 | Yabuki | |
| 2014/0374476 A1 | 12/2014 | Ban | |
| 2016/0110583 A1 | 4/2016 | Kuo | |
| 2016/0294555 A1 | 10/2016 | Jakobsson | |
| 2018/0089483 A1 * | 3/2018 | Norimatsu | G06V 40/1376 |
| 2018/0089484 A1 * | 3/2018 | Satou | A61B 5/117 |
| 2018/0173936 A1 * | 6/2018 | Mizoguchi | G06T 7/00 |
| 2019/0005302 A1 * | 1/2019 | Mizoguchi | G06F 21/32 |
| 2019/0005303 A1 * | 1/2019 | Mizoguchi | G06V 40/1388 |
| 2019/0006302 A1 | 1/2019 | Mizoguchi | G06V 40/1394 |
| 2019/0019010 A1 * | 1/2019 | Mizoguchi | G06T 7/00 |
| 2021/0133414 A1 * | 5/2021 | Norimatsu | G06T 11/20 |
| 2021/0326552 A1 * | 10/2021 | Satou | G06V 40/1359 |
| 2023/0127598 A1 * | 4/2023 | Satou | G06V 40/1359 |
| | | | 382/125 |
| 2024/0412555 A1 * | 12/2024 | Satou | G06V 40/1376 |

FOREIGN PATENT DOCUMENTS

| | | |
|---|---|---|
| JP | 2000-057343 A | 2/2000 |
| JP | 2005-346222 A | 12/2005 |
| JP | 2005-352712 A | 12/2005 |
| JP | 2011-48602 A | 3/2011 |
| JP | 2013-171325 A | 9/2013 |
| WO | 2011/052036 A1 | 5/2011 |
| WO | 2011/058836 A1 | 5/2011 |

OTHER PUBLICATIONS

Carsten, et al., "Improving fingerprint alteration detection", 9th International Symposium on Image and Signal Processing and Analysis (ISPA) IEEE, Zagreb, Croatia, Sep. 7, 2015, pp. 83-86 (4 pages total).

Communication dated Nov. 13, 2018, from the European Patent Office in counterpart European Application No. 16772933.4.

Decision to Grant a Patent dated Dec. 1, 2020 from the Japanese Patent Office in Application No. 2017-510082.

International Search Report for PCT/JP2016/060336 dated May 24, 2016 [PCT/ISA/210].

Maltoni, et al., "Fingerprint Classification and Indexing", Handbook of Fingerprint Recognition, Jan. 1, 2009, Springer, London, GB, pp. 235-269 (35 pages total).

Written Opinion for PCT/JP2016/060336 dated May 24, 2016 [PCT/ISA/237].

Yoon, et al., "Altered Fingerprints: Analysis and Detection", IEEE Transactions on Pattern Analysis and Machine Intelligence, IEEE Computer Society, USA, Mar. 1, 2012, vol. 34, No. 3, pp. 451-464 (14 pages total).

Asker M. Bazen, "Fingerprint Identification—Feature Extraction, Matching, and Database Search" Twente University Press, Aug. 19, 2002, 181 pages.

Japanese Office Action for JP Application No. 2020-219680 mailed on Jan. 4, 2022 with English Translation.

Miyuki Miki et al., "Improvement of the Binarization Method for Fingerprint Images with Injury", Transactions of Information Processing Society of Japan, vol. 43, No. 12, Information Processing Society of Japan, Dec. 15, 2002, pp. 4042-4050, Japan.

* cited by examiner

BIOLOGICAL PATTERN INFORMATION PROCESSING DEVICE, BIOLOGICAL PATTERN INFORMATION PROCESSING METHOD, AND PROGRAM

CROSS REFERENCE TO RELATED APPLICATIONS

This application is a continuation of U.S. application Ser. No. 18/078,232, filed Dec. 9, 2022, which is a continuation of U.S. application Ser. No. 17/364,164, filed Jun. 30, 2021, which issued as U.S. Pat. No. 11,557,146, which is a continuation of U.S. application Ser. No. 15/563,211, filed Sep. 29, 2017, which issued as U.S. Pat. No. 11,055,511, which is a National Stage of International Application No. PCT/JP2016/060336 filed Mar. 30, 2016, claiming priority based on Japanese Patent Application No. 2015-074479 filed Mar. 31, 2015, the contents of all of which are incorporated herein by reference in their entirety.

TECHNICAL FIELD

The present invention relates to a biological pattern information processing device, a biological pattern information processing method, and a program.

BACKGROUND ART

In recent years, biometric authentication has attracted attention as one of the authentication methods for identifying individuals. A biometric pattern such as a fingerprint has a feature that it does not change even after years of time, and is highly reliable for authentication. Meanwhile, still there is a possibility of unauthorized acts using false biometric patterns such as false fingers, and techniques for preventing such unauthorized acts have also been developed.

For example, the technique disclosed in Patent Document 1 is a technique for determining a false finger with a transparent thin film attached on the surface of a finger. Patent Document 1 discloses a technique of classifying an image region into a plurality of regions including at least a skin region and a background region by using colors of pixels included in a captured image, and using a characteristic of a region that is not classified either as the skin region or as the background region, to thereby determine whether or not a foreign object is present around a finger. According to this technique of Patent Document 1, a foreign object around a finger (a portion having a biological pattern) can be detected.

PRIOR ART DOCUMENTS

Patent Documents

[Patent Document 1] International Publication No. WO 2011/058836

DISCLOSURE OF THE INVENTION

Problem to be Solved by the Invention

However, in order to prevent unauthorized acts related to authentication that uses biometric pattern information, there are some cases where foreign object (for example, a thin film or the like) detection alone based on color information of pixels is insufficient.

For example, in recent years, cases have been found in which biological patterns (for example, fingerprints) are damaged due to surgical operations, burns, or the like. In this type of cases, even if a preliminarily registered biometric pattern is damaged, an ability to perform correct verification or at least detection of the presence of damage is required. In addition, it is required to present the detected damage to the user in an easy-to-understand manner.

The present invention has been made based on the problem recognition above. An exemplary object of the present invention is to provide a biological pattern information processing device, a biological pattern information processing method, and a program that are capable of detecting a singular region, even when a biological pattern has a singular region due to damage or the like.

Means for Solving the Problem

A biological pattern information processing device according to an exemplary aspect of the present invention includes: a biological pattern information acquisition unit that acquires biological pattern information indicating a biological pattern; and a singular region detection unit that detects a singular region including damage, from the biological pattern indicated by the acquired biological pattern information.

In the above-described biological pattern information processing device, the biometric pattern information may include information indicating a fingerprint image, the singular region detection unit may detect a directional singular point of a ridge line from the fingerprint image, and the singular region detection unit may detect the singular region based on a condition of number of the directional singular point for each of types, or a condition of a positional relationship between the types of the directional singular point.

In the above-described biological pattern information processing device, the biometric pattern information may include information indicating a fingerprint image, the singular region detection unit may acquire a plurality of pieces of ridge line direction information respectively corresponding to a plurality of portions included in the fingerprint image, the singular region detection unit may find an evaluation value for each of the plurality of pieces of ridge line direction information, based on a correlation between each of the plurality of pieces of ridge line direction information and an abnormal ridge line directional pattern template that is preliminarily held, the evaluation value representing a degree of possession of an abnormal ridge line directional pattern, and the singular region detection unit may detect, as the singular region, a portion corresponding to a piece of ridge direction information in which the evaluation value is equal to or greater than a predetermined threshold value.

In the above-described biological pattern information processing device, the biometric pattern information may include information indicating a fingerprint image, the singular region detection unit may acquire a plurality of pieces of ridge line direction information respectively corresponding to a plurality of regions included in the fingerprint image, the singular region detection unit may obtain smoothed ridge line direction information by performing a direction smoothing process for each of the plurality of pieces of ridge line direction information based on ridge line direction information corresponding to a region positioned around the region corresponding to the ridge line direction information, and the singular region detection unit may detect, as the singular region, the region corresponding to the ridge line direction information in which a difference between the ridge line direction information and the smoothed ridge line direction information is greater than a predetermined threshold value.

In the above-described biological pattern information processing device, the biometric pattern information may include information indicating a fingerprint image, the singular region detection unit may acquire a plurality of pieces of ridge line direction information and a plurality of pieces of ridge line pitch information respectively corresponding to a plurality of regions included in the fingerprint image, the singular region detection unit may find an evaluation value based on the plurality of pieces of ridge line direction information and the plurality of pieces of ridge line pitch information, the evaluation value taking a greater value as a difference in ridge line directions and a difference in ridge line pitches become greater between adjacent regions in the fingerprint image, and in a case where the evaluation value is greater than a predetermined threshold value, the singular region detection unit may detect the adjacent regions as being the singular region by a cutting-off process.

The above-described biological pattern information processing device may further include: a collation unit that collates biological pattern information corresponding to a region other than the detected singular region among the acquired biological pattern information, with pre-registered biological pattern information which is biological pattern information registered preliminarily in association with identification information for identifying an individual.

In the above-described biological pattern information processing device, in a case of performing the collation, the collation unit may make at least one of a positional deviation allowance and a mismatch allowance to be allowed to vary, the positional deviation allowance representing a degree to which positional deviation is allowed, and the mismatch allowance representing a degree to which a mismatch is allowed are variable.

The above-described biological pattern information processing device may further include: a repair unit that repairs damage in biological pattern information corresponding to the singular region in the acquired biological pattern information. The collation unit performs the collation by regarding a region corresponding to the repaired biological pattern information as a region other than the singular region.

In the above-described biological pattern information processing device, the biometric pattern information may be information including a fingerprint image, and the repair unit may repair the damage by excluding, from the fingerprint image, an exclusion region defined based on the singular region.

In the above-described biological pattern information processing device, the biological pattern information may be information including a fingerprint image, the repair unit may find an evaluation value for each of a plurality of portions included in the fingerprint image, based on a correlation between ridge line direction information and an abnormal ridge line directional pattern template that is preliminarily held, the evaluation value representing a degree to which the ridge line direction information has an abnormal ridge line directional pattern, the repair unit may extract a linear component of the evaluation value in the fingerprint image, and the repair unit may repair the damage by mutually replacing fingerprint images included in a first polygon and a second polygon determined based on the extracted linear component.

A biological pattern information processing method according to an exemplary aspect of the present invention includes: acquiring biological pattern information indicating a biological pattern; and detecting a singular region including damage, from the biological pattern indicated by the acquired biological pattern information.

A program according to an exemplary aspect of the present invention causes a computer to execute: acquiring biological pattern information indicating a biological pattern; and detecting a singular region including damage, from the biological pattern indicated by the acquired biological pattern information.

Effect of the Invention

According to the present invention, when a biological pattern has a singular region such as damage, the singular region can be detected. This leads to being able to perform a collation process while preventing degradation of accuracy due to the singular region.

EMBODIMENTS FOR CARRYING OUT THE INVENTION

Next, several exemplary embodiments of the present invention will be described with reference to the drawings.

First Exemplary Embodiment

Figure 1:
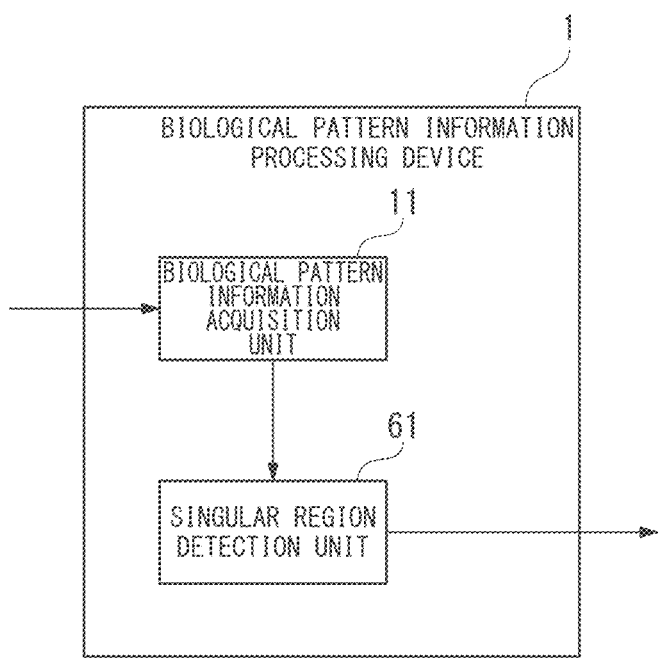
FIG. 1 is a block diagram showing a schematic functional configuration of a biological pattern information processing device according to a first exemplary embodiment.

FIG. 1 is a block diagram showing a schematic functional configuration of a biological pattern information processing device according to a first exemplary embodiment. As shown in FIG. 1, a biological pattern information processing device 1 according to the present exemplary embodiment includes a biological pattern information acquisition unit 11 and a singular region detection unit 61. The biological pattern information acquisition unit 11 may be hereinafter referred to as an information acquisition unit 11 in some cases.

The information acquisition unit 11 acquires biological pattern information from the outside.

The singular region detection unit 61 performs a process of detecting a singular region based on the biological pattern information acquired by the information acquisition unit 11. Then, the singular region detection unit 61 outputs information indicating whether a singular region is detected (presence or absence of a singular region) and information on the position of the singular region when a singular region is detected (position information indicating a range of the singular region). Details of the determination process performed by the singular region detection unit 61 will be described later.

The singular region is a region where singular biological pattern information due to a part of the living body being damaged is present (a damaged part) or a region where the biological pattern information is distorted due to wrinkles or the like on the surface of the living body. In the singular region, there is a possibility that a pattern different from the pattern originally possessed by the living body is present. Examples of the cause of living body damage causing a singular region to occur include cuts, scratches, etc., burns, and burn sores due to chemicals (for example, strong acids, etc.).

A typical example of the biological pattern information handled by the biological pattern information processing device 1 is fingerprint information. A fingerprint is a pattern formed by ridge lines on the surface of a finger or a toe. Human skin is formed by overlapping of epidermis and dermis. The epidermis is present on the surface side (outside), and the dermis is present on the far side (inside). A layer called a papillary layer exists in the portion where the epidermis and the dermis are in contact with each other. In the vicinity of this papillary layer, concaves and convexes are present on the dermis side, and this convex part forms ridge lines. Sweat gland pores are aligned along the convex part of the ridge line. The ridge line pattern formed on the dermis side can also be seen as it is on the epidermis side. This pattern is generally called a fingerprint. Even if the epidermis is damaged, as long as the ridge line structure in the dermis is maintained, when the epidermis is regenerated, a pattern based on the ridge line structure of the original dermis side is reproduced also on the epidermis side. In this case, the biological pattern information processing device 1 treats fingerprint image information obtained as a two-dimensional image as biological pattern information.

Another example of the biological pattern information is not the fingerprint itself but an arrangement pattern of blood capillaries and sweat gland pores near the surface of the finger.

When the biological pattern information to be handled is limited to a fingerprint image, the biological pattern information processing device may be called a "fingerprint processing device".

Specific methods for acquiring fingerprints vary as follows. It is possible to select them appropriately from among these methods.

The first method of acquiring a fingerprint is a method in which the epidermis of a finger having a fingerprint is image-captured by a camera or the like and information on the image is acquired as biological pattern information.

The second method of acquiring a fingerprint is a method of acquiring a distribution of electrical characteristics of the surface of a finger as biological pattern information by using a sensor in contact with the living body. The electrical characteristics of the surface of a finger vary from part to part depending on, for example, the shape of the ridge lines and the presence or absence of sweat gland pores, and it is possible to acquire a two-dimensional distribution of such characteristics as pattern information.

The third method of acquiring a fingerprint is a method of transferring a substance such as ink attached to a finger to a medium such as paper and reading the image obtained on the medium with an optical scanner or the like.

The fourth method of acquiring a fingerprint is a method of acquiring a pattern of the surface of a finger (living body) by using a technique of OCT (optical coherency tomography). The OCT is a method of acquiring mutual interference caused by the phase difference between light reflected from an observation target as a result of shining it on the observation target and a reference light, as a pattern image of light intensity. In the case of using the OCT, by appropriately changing the wavelength of light, not only information on the surface of a finger but also information of a pattern inside of the living body at certain depths (depths of approximately several hundreds of micrometers to 2,000 micrometers) can be acquired. In this way, not only the surface but also a pattern inside the living body can be used as biological pattern information. Examples of information on patterns inside a living body that can be used include ridge line patterns in the dermis, arrangement patterns of the sweat gland pores, and arrangement patterns of the blood capillaries. When acquiring information of a pattern inside a living body using the OCT, for example, it is used as information of a two-dimensional image for each cross section at a predetermined depth. Alternatively, it is also possible to use three-dimensional biological pattern information obtained by superimposing a number of two-dimensional images from each of these cross sections.

When three-dimensional information is not included, fingerprint information is represented as a two-dimensional image. Also, when only information about a certain layer is extracted from three-dimensional information, that information can be expressed as a two-dimensional image. Hereinafter, these two-dimensional images may be referred to as "fingerprint images" in some cases.

(Regarding Method of Singular Region Detection Processing)

In the following, an internal configuration of the singular region detection unit 61 and a method of singular region detection processing will be described. Here, target biological pattern information is information of a fingerprint image.

Figure 2:
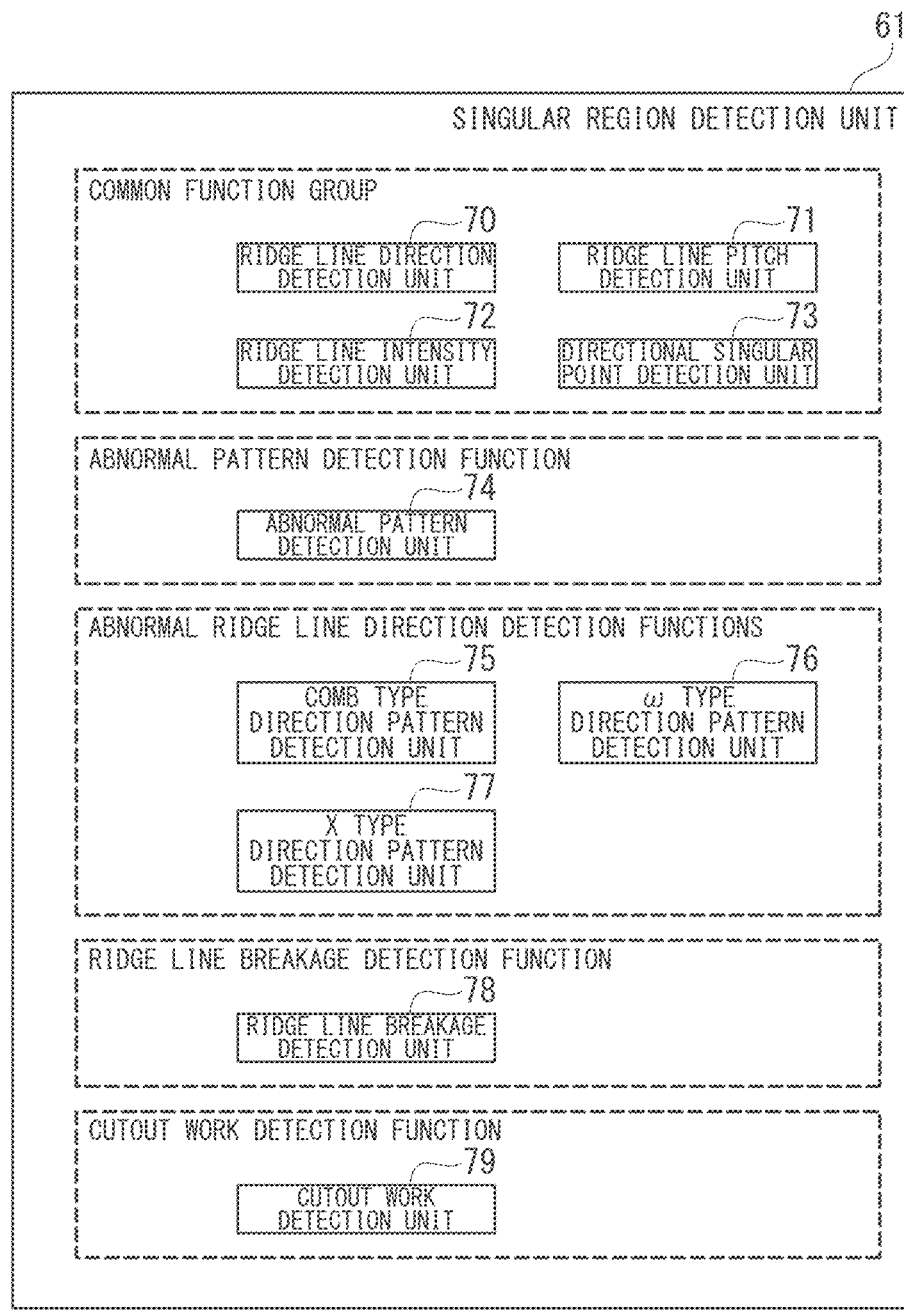
FIG. 2 is a block diagram showing a schematic functional configuration inside a singular region detection unit according to the first exemplary embodiment.

FIG. 2 is a block diagram showing a schematic functional configuration inside the singular region detection unit 61. As shown in FIG. 2, the singular region detection unit 61 includes a common function group, an abnormal pattern detection function, an abnormal ridge line direction detection function, a ridge line breakage detection function, and a cutout work detection function. The common function group includes a ridge line direction detection unit 70, a ridge line pitch detection unit 71, a ridge line intensity detection unit 72, and a direction singular point detection unit 73. The operation of the singular region detection unit 61 using these functions will be described below.

The singular region detection unit 61 first receives data of a fingerprint image from the singular region detection result acquisition unit 12.

The singular region detection unit 61 analyzes the received fingerprint image using functions included in the common function group thereof. Specifically, the ridge line direction detection unit 70 detects a ridge line direction in the fingerprint image. Further, the ridge line pitch detection unit 71 detects a ridge line pitch in the fingerprint image. Moreover, the ridge line intensity detection unit 72 detects a ridge line intensity in the fingerprint image. In addition, the direction singular point detection unit 73 detects a directional singular point in the fingerprint image. The singular region detection unit 61 may detect only one of a ridge line direction, a ridge line pitch, a ridge line intensity, and a direction singularity, but not all of them. The process itself of detecting these ridge line pitch, ridge line intensity, and directional singular point from the fingerprint image is a feature extraction process in a general fingerprint authentication technique and can be performed using existing techniques.

A ridge line direction is a direction in which the ridge is oriented. A ridge line pitch is a width of parallel ridge lines (a distance from one ridge line to another parallel adjacent ridge line). A ridge line intensity is a degree indicating the likelihood of being a ridge line as information obtained from an image. A directional singular point is a portion where a ridge line direction becomes discontinuous in a fingerprint image.

The singular region detection unit 61 first extracts a ridge line direction, a ridge line pitch, and a ridge line intensity from the received fingerprint image using Gabor filters. Specifically, the singular region detection unit 61 applies the Gabor filters in which the direction and pitch are stepwise changed for each pixel included in the fingerprint image, and the direction and the pitch of the filter that yields the highest absolute value among these applied Gabor filters is regarded as the ridge line direction and the pitch at that pixel. In addition, the singular region detection unit 61 extracts the absolute value of the filter applied value at that time as the ridge line intensity.

Further, the singular region detection unit 61 detects a directional singular point in the fingerprint image. At a directional singular point there exists a directional shape called a delta and a directional shape called a core. Of these, the core can be further classified into a true circular core and a semicircular core. A true circular core is a core whose ridge line rotates 360 degrees around the directional singular point. A semicircular core is a core whose ridge line rotates 180 degrees around the directional singular point. As a method of detecting a directional singular point, the singular region detection unit 61 uses an existing technique. As an example, a method for detecting a directional singular point is also disclosed in the literature [Asker Michel Bazen, "Fingerprint identification: Feature Extraction, Matching, and Database Search", Twente University Press, 2002]. For each finger, the singular region detection unit 61 stores the number of each of the detected true circular cores, semicircular cores, and deltas and the position (coordinates) of the directional singular point of each of these, for processing in a later step. Moreover, the singular region detection unit 61 detects the direction of the pattern at the directional singular point (for example, in the case of a semicircular core, whether the side on which the ridge line is open is the upper side or the lower side of the finger), and stores the information for processing in a later step.

In addition to the example of the existing technique mentioned above, the singular region detection unit 61 may use another method. In order to improve the accuracy, the singular region detection unit 61 may also use in combination another means for correcting extraction errors in ridge line direction and ridge line pitch.

Next, the singular region detection unit 61 performs processing for detecting four types of singular regions in the fingerprint image. The four types are (1) abnormal pattern, (2) abnormal ridge line direction, (3) ridge line breakage, and (4) cutout work. The features of the fingerprints having these four types of abnormality and the detection methods thereof will be described below.

((1) Abnormal Pattern Detection)

The singular region detection unit 61 includes an abnormal pattern detection unit 74 as a function for detecting an abnormal pattern. The abnormal pattern detection unit 74 detects an abnormal pattern based on the number and positional relationship of the directional singular points (delta, semicircular core, perfect circle core) detected above. Normal fingerprint images are classified into four types of patterns from the ridge line direction patterns. The four types are arch-shaped pattern, loop-shaped pattern, spiral-shaped pattern, and variant-shaped pattern. For each of these patterns, the number and positional relationship of the directional singular points are defined.

Specifically, in the arch-shaped pattern, the number of cores is 0 and the number of deltas is also 0. That is to say, the curve of the ridge line is smooth. In the loop-shaped pattern, the number of semicircular cores is 1, and the number of deltas is 1 or less. In the spiral-shaped pattern, either the number of circular cores is 1 and the number of deltas is 2 or less, or the number of semicircular cores is 2 and the number of deltas is 2 or less. In the variant-shaped pattern, either the number of semicircular cores is 3 and the number of deltas is 3 or less, or the number of circular cores is 1, the number of semicircular cores is 1, and the number of deltas is 3 or less. In the case of a normal fingerprint image, the positional relationship of the directional singular point also has a predetermined restriction.

Normal fingerprint images have the above patterns. The abnormal pattern detection unit 74 detects an abnormal pattern image that cannot appear in a normal fingerprint image as an abnormal pattern. Specifically, the singular region detection unit 61 detects the fingerprint image as an abnormal pattern when any one of the following conditions (A) to (F) is satisfied.

Condition (A): When there are two or more circular cores
Condition (B): When there are four or more semicircular cores
Condition (C): When two or more semicircular cores are present and one or more circular cores are also present
Condition (D): When there are four or more deltas
Condition (E): Delta is present above the core (on the side near the fingertip)
Condition (F): When there are two or more semicircular cores on the upper side That is to say, the singular region detection unit 61 detects the directional singular point of the ridge line included in the fingerprint image, and detects a singular region based on the condition of the number of each directional singular point type or the condition of the positional relationship between the types of the directional singular points.

One of the reasons why these types of abnormal patterns are detected in fingerprints is a surgical treatment applied to the finger.

Figure 3A:
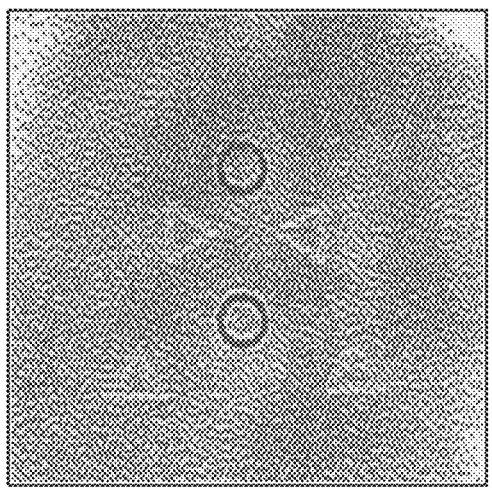
FIG. 3A is a schematic diagram showing an example of an abnormal pattern in a fingerprint to be detected by the singular region detection unit according to the first exemplary embodiment.
Figure 3B:
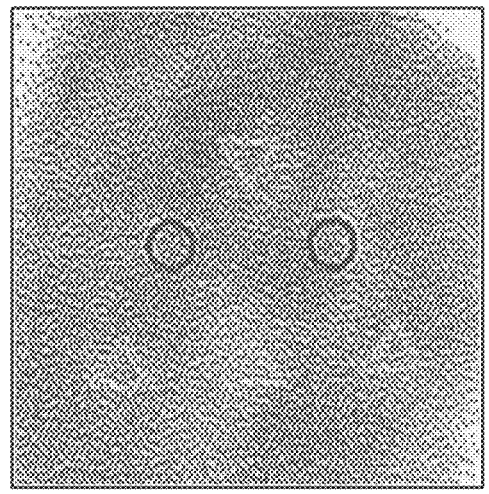
FIG. 3B is a schematic diagram showing an example of an abnormal pattern in a fingerprint to be detected by the singular region detection unit according to the first exemplary embodiment.
Figure 3C:
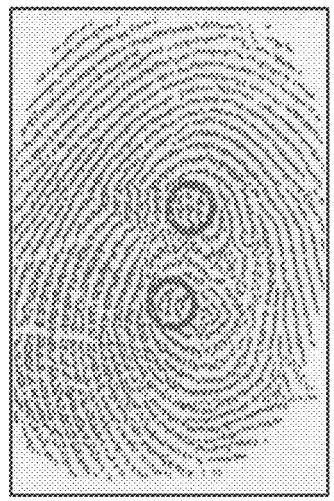
FIG. 3C is a schematic diagram showing an example of an abnormal pattern in a fingerprint to be detected by the singular region detection unit according to the first exemplary embodiment.

FIG. 3A to FIG. 3C show examples of abnormal patterns in fingerprints. In FIG. 3A to FIG. 3C, the circled portions are circular cores. Also, the portions indicated by triangles are deltas. The example of the fingerprint image shown in FIG. 3A has two circular cores and four deltas. That is to say, this fingerprint image meets the above conditions (A) and (D), and the abnormal pattern detection unit 74 determines that it has an abnormal pattern. The example of the fingerprint image shown in FIG. 3B has two circular cores and four deltas. Also, in the example of FIG. 3B, a delta exists above the two circular cores. That is to say, this fingerprint image meets the above conditions (A), (D), and (E), and the abnormal pattern detection unit 74 determines that it has an abnormal pattern. The example of the fingerprint image shown in FIG. 3C has two circular cores. That is to say, this fingerprint image meets the above condition (A), and the abnormal pattern detection unit 74 determines that it has an abnormal pattern.

If an abnormal pattern is detected, the abnormal pattern detection unit 74 outputs the type of the abnormality (any of the conditions (A) to (F) above) and the position and type of the directional singular point concerning the abnormality.

Further, if an abnormal pattern is not detected, the abnormal pattern detection unit 74 outputs information indicating that an abnormal pattern is not detected.

((2) Abnormal Ridge Line Direction Detection)

The singular region detection unit 61 detects an abnormal pattern in the ridge line direction. There are several patterns also in abnormal ridge line directions. Typical three types of patterns are called comb type direction pattern, ω type direction pattern, and X type direction pattern for convenience. In the present exemplary embodiment, the singular region detection unit 61 detects three types of abnormal ridge line directions, namely the comb type direction pattern, the ω type direction pattern, and the X type direction pattern. There is a possibility that these types of abnormal ridge line direction patterns may be observed at a boundary portion of the transplanted epidermis part if a fingerprint epidermis transplant operation or the like has been performed. These patterns cannot be seen in normal fingerprint images.

Figure 4A:
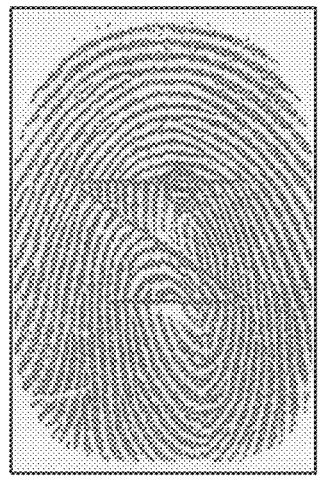
FIG. 4A is a schematic diagram showing an example of a fingerprint image including an abnormal ridge line direction to be detected by the singular region detection unit according to the first exemplary embodiment.
Figure 4B:
FIG. 4B is a schematic diagram showing an example of a fingerprint image including an abnormal ridge line direction to be detected by the singular region detection unit according to the first exemplary embodiment.
Figure 4C:
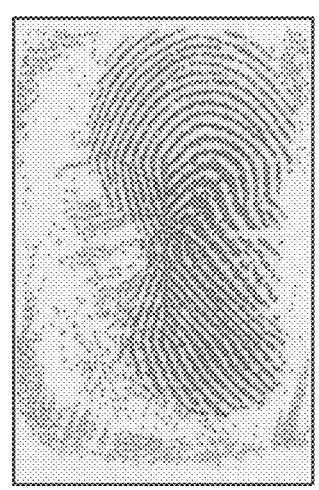
FIG. 4C is a schematic diagram showing an example of a fingerprint image including an abnormal ridge line direction to be detected by the singular region detection unit according to the first exemplary embodiment.

FIG. 4A to FIG. 4C show examples of fingerprint images including abnormal ridge line directions.

FIG. 4A is an example of a fingerprint image having an abnormal ridge line direction called a comb type direction pattern. This comb type abnormal ridge line direction is a ridge line direction pattern which is likely to occur near the boundary of the transplanted epidermis when the fingerprint epidermis is cut and removed with a scalpel, and a surgical operation such as changing the position and replacement is performed.

FIG. 4B is an example of a fingerprint image having an abnormal ridge line direction called a ω type direction pattern. This ω type abnormal ridge line direction is also a ridge line direction pattern which is likely to occur near the boundary of the transplanted epidermis when the fingerprint epidermis is cut and removed with a scalpel, and a surgical operation such as s changing the position and replacement is performed. In addition, the ω type direction pattern is a pattern which is likely to occur also when a deep cut is made to the arch-shaped portion of the fingerprint with a blade or the like.

FIG. 4C is an example of a fingerprint image having an abnormal ridge line direction called an X type direction pattern. This abnormal ridge line direction of the X type is a ridge line direction pattern which is likely to occur in the stitched portion when the skin is tightly stitched with a surgical thread or the like.

Figure 5A:
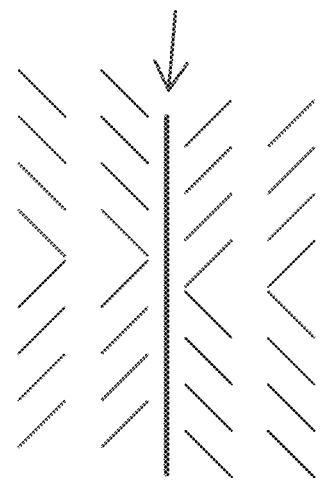
FIG. 5A is a conceptual diagram schematically showing a template used by the singular region detection unit according to the first exemplary embodiment and corresponding to an abnormal ridge line directional pattern (X type).
Figure 5B:
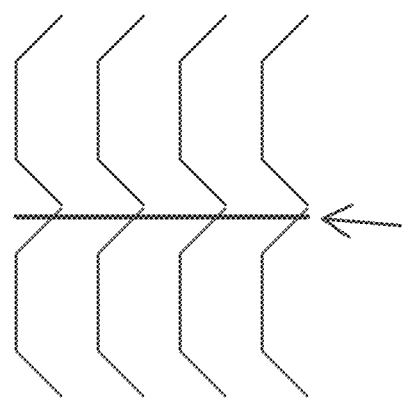
FIG. 5B is a conceptual diagram schematically showing a template used by the singular region detection unit according to the first exemplary embodiment and corresponding to a (ω type) of an abnormal ridge line directional pattern.
Figure 5C:
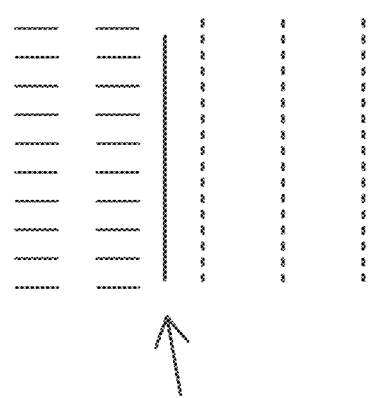
FIG. 5C is a conceptual diagram schematically showing a template used by the singular region detection unit according to the first exemplary embodiment and corresponding to an abnormal ridge line directional pattern (comb type).

FIG. 5A to FIG. 5C are conceptual diagrams schematically showing templates corresponding to each of the abnormal ridge line direction patterns (comb type, ω type, and X type).

FIG. 5A corresponds to the X type direction pattern in the fingerprint image.

FIG. 5B corresponds to the ω type direction pattern in the fingerprint image.

FIG. 5C corresponds to the comb type direction pattern in the fingerprint image.

The singular region detection unit 61 includes, in the interior thereof, a comb type direction pattern detection unit 75, a ω type direction pattern detection unit 76, and an X type direction pattern detection unit 77 in correspondence with the abnormal direction patterns described above. The singular region detection unit 61 performs processing for detecting these abnormal direction patterns by using information on the ridge line direction and information on the ridge line intensity already detected by the above method.

A processing method for detecting each of the abnormal direction patterns will be described below.

The comb type direction pattern detection unit 75 calculates and outputs the degree indicating the likelihood of the comb type direction pattern of the fingerprint image using the data input of the ridge line direction and the ridge line intensity preliminarily detected based on the given fingerprint image.

Specifically, the comb type direction pattern detection unit 75 preliminarily holds comb type template data representing the direction pattern as shown in FIG. 5C in the internal memory. The comb type template data is data obtained on the basis of a fingerprint image having the comb type direction pattern, and is stored in a two dimensional array corresponding to polar coordinates. "i" which is the first index of comb template data Tk(i, j) which is a two dimensional array, corresponds to the displacement angle around the center of the template data. "i=1, 2, . . . , M" is satisfied. This "i" is an index value corresponding to each direction when 360 degrees in all directions from the center of the fingerprint image are cut in increments of (360/M) degrees. Where the positive direction of the x-axis of the xy orthogonal coordinate system is 0 degrees, the counterclockwise direction is the positive direction of the displacement angle. Moreover, a second index "j" corresponds to the distance from the center of the fingerprint image. "j=1, 2, . . . , N" is satisfied. This "j" is an index value corresponding to the distance from the center of the template. The value of each element of Tk (i, j) is a two dimensional vector (unit vector) value representing the ridge line direction in the portion (small region) represented by this polar coordinate.

The comb type direction pattern detection unit 75 calculates the maximum value of the sum of the inner products of the template direction Tk (k, t) and the direction vectors in the ridge line direction within the circle of the image while changing the template rotation angle t, with respect to an arbitrary pixel position (x, y) in the given fingerprint image. The maximum value is expressed by Ek (x, y) according to the following equation.

$$Ek(x, y) = \max_{t=1,\ldots,M} \left\{ \sum_{i=1}^{N} \frac{Tk(t, i) \cdot Td(x + dx(i), y + dy(i))}{N} \right\} \quad \text{(Equation 1)}$$

In Equation (1) above, Id (x, y) is a unit vector representing the ridge line direction at a coordinates (x, y) of the fingerprint image. Tk (t, i) is the i-th direction of the comb template (rotation angle is t). dx (i) is the x coordinate displacement of the i-th element in the template. dy (i) is the y coordinate displacement of the i-th element in the template.

That is to say, the value of Ek (x, y) calculated by this Equation (1) is a correlation value when correlation between the fingerprint image and the template is the greatest (when t corresponds to such an angle) where the template is rotated 360 degrees at the coordinates (x, y) of the fingerprint image.

Also, at this time, the ridge line direction (displacement angle) is expressed as a numerical value in the range up to 180 degrees in the counterclockwise direction where the X axis positive direction is taken as 0 degree. However, since the 0 degree direction and the 180 degrees direction need to be regarded as substantially the same direction, the inner product is yielded upon converting the angle of the direction vector so that the angle formed thereby with the X axis positive direction (0 degree direction) is doubled.

The value of Ek (x, y) calculated by the Equation (1) above is an index representing the directional consistency between the fingerprint image and the template. Further, the comb type direction pattern detection unit 75 calculates a comb type evaluation value Wk (x, y) multiplied by the ridge line intensity. The ridge line intensity represents fingerprint likeness.

$$Wk(x, y) = \max(0, Ek(x, y) - C) \times Is(x, y) \quad \text{(Equation 2)}$$

In the above equation, C is an appropriately set threshold value. That is to say, the threshold value C has an effect of removing a portion where the value of Ek (x, y) is equal to or less than C as noise. Is (x, y) is an average value of the ridge line intensity within the same radius as the template where the coordinates (x, y) serves as the center. That is to say, the evaluation value Wk (x, y) is obtained by subtracting the threshold value C from the value of Ek (x, y) (in the case where the result becomes negative, it is set to 0) and further multiplying by the ridge line intensity in the vicinity of the coordinate (x, y).

The comb type direction pattern detection unit 75 outputs this calculated value Wk (x, y) as a comb type abnormality degree. This comb type abnormality degree is a degree indicating the likelihood of a comb type direction pattern.

The ω type direction pattern detection unit 76 preliminarily holds ω type template data representing the direction pattern as shown in FIG. 5B in the internal memory. The data structure of the ω type template data itself is similar to that of the comb type template data. The ω type template data is template data representing a ridge line direction, and is preliminarily created based on an actual fingerprint image having a ω type direction pattern. Based on the given fingerprint image and the ω type template data above, the ω type direction pattern detection unit 76 calculates a ω type abnormality degree Wo (x, y) by using the same procedure as that of the above calculation procedure of the comb type direction pattern detection unit 75.

The X type direction pattern detection unit 77 preliminarily holds X type template data representing the direction pattern as shown in FIG. 5A in the internal memory. The data structure of the X type template data itself is similar to that of the comb type template data. The X type template data is template data representing a ridge line direction, and is preliminarily created based on an actual fingerprint image having an X type direction pattern. Based on the given fingerprint image and the X type template data above, the X type direction pattern detection unit 77 calculates an X type abnormality degree Wx (x, y) by using the same procedure as that of the above calculation procedure of the comb type direction pattern detection unit 75.

The singular region detection unit 61 determines whether or not it is an abnormal ridge line direction fingerprint based on whether or not each maximum value of the comb type abnormality degree Wk (x, y) output from the comb type direction pattern detection unit 75, the ω type abnormality degree Wo (x, y) output from the ω type direction pattern detection unit 76, and the X type abnormality degree Wx (x, y) output from the X type direction pattern detection unit 77, exceeds a predetermined threshold. If the value exceeds the threshold value, the singular region detection unit 61 determines that the fingerprint image is an abnormal ridge line direction fingerprint (that is to say, a comb type direction pattern, a ω type direction pattern, or an X type direction pattern). In other cases, it is determined that it is not an abnormal ridge line direction fingerprint.

As another method, the singular region detection unit 61 may determine whether or not it is an abnormal ridge line direction fingerprint based on whether or not the sum of each maximum value of the comb type abnormality degree Wk (x, y) output from the comb type direction pattern detection unit 75, the ω type abnormality degree Wo (x, y) output from the ω type direction pattern detection unit 76, and the X type abnormality degree Wx (x, y) output from the X type direction pattern detection unit 77, exceeds a predetermined threshold. When the value exceeds the threshold value, the singular region detection unit 61 determines that the fingerprint image is an abnormal ridge line direction fingerprint. The singular region detection unit 61 determines that it is not an abnormal ridge line direction fingerprint in other cases.

That is to say, the singular region detection unit 61 acquires ridge line direction information for each portion included in the fingerprint image. Moreover, the singular region detection unit 61 finds an evaluation value indicating the extent to which the ridge line direction information has an abnormal ridge line direction pattern, based on the correlation between the ridge line direction information, and the template of the abnormal ridge line direction pattern held preliminary (such as the comb type direction pattern, the ω type direction pattern, and the X type direction pattern). Further, when the evaluation value is equal to or greater than the predetermined threshold value, the singular region detection unit 61 detects a portion corresponding to the ridge line direction information as a singular region.

When it is determined that it is an abnormal ridge line direction fingerprint, the singular region detection unit 61 outputs the information on the position of the singular region.

Weighting may be performed with a probability distribution of each evaluation value (comb type abnormality degree, ω type abnormality degree, and X type abnormality degree) based on an actual fingerprint database. Thereby, the determination accuracy of the singular region detection unit 61 can be further enhanced.

In the present exemplary embodiment, the singular region detection unit 61 includes the comb type direction pattern detection unit 75, the ω type direction pattern detection unit 76, and the X type direction pattern detection unit 77 in the interior thereof, and detects the abnormal ridge line direction corresponding thereto. However, it is not limited to this type of configuration. The configuration may omit some of these.

Conversely, there may be provided templates of other direction patterns to detect abnormal ridge line directions other than these three types. As an example, it is possible to adopt a configuration capable of detecting a pattern slightly changing the ridge line angle of the comb type, the ω type, and the X type, or a configuration capable of detecting several types of patterns as a result of changing the radius of the template.

The above method of detecting a singular region based on the number of directional singular points and the positional relationship between directional singular points, described as "(1) Abnormal Pattern Detection", is an effective technique when a clear image of an entire fingerprint is obtained. On the other hand, in the present method ((2) Abnormal Ridge Line Direction Detection) that uses evaluation values based on a template, there is an advantage that it enables detection of an abnormal fingerprint of a specific shape even when only an image of only a fraction of the fingerprint is acquired.

((3) Ridge Line Breakage Detection)

The singular region detection unit 61 also has a function of detecting breakage of a ridge line in the fingerprint. Specifically, the singular region detection unit 61 includes, in the interior thereof, a ridge line breakage detection unit 78. The singular region detection unit 61 performs processing for detecting these abnormal direction patterns by using information on the ridge line direction and information on the ridge line intensity already detected by the above method.

Figure 6:
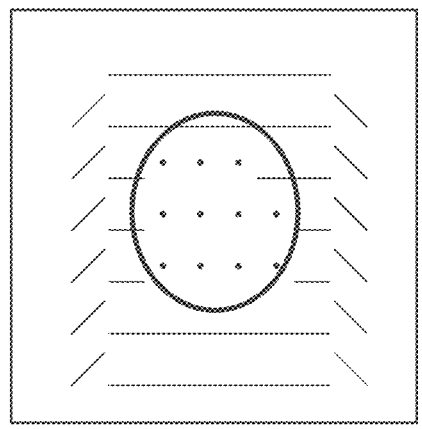
FIG. 6 is a schematic diagram conceptually showing an example of a fingerprint image including ridge line breakage to be detected by the singular region detection unit according to the first exemplary embodiment.

FIG. 6 is an example conceptually showing a fingerprint image including ridge line breakage. In the example of the fingerprint image shown in FIG. 6, a part of the ridge lines which were originally continuous is discontinuous, and there is a dotted pattern in that part. In FIG. 6, a portion indicated by an elliptical frame is a portion that includes ridge line breakage. This type of ridge line breakage can be caused by burns or chemical damage.

The ridge line breakage detection unit 78 acquires the data of the ridge line direction image acquired by the above-described method. This ridge line direction image data includes ridge line direction data at each pixel. Then, the ridge line breakage detection unit 78 executes a direction smoothing process over a large area. This direction smoothing process is a process of correcting a portion in the fingerprint image including the ridge line direction detected in error due to noise or the like, to the correct ridge line direction. The direction smoothing processing itself can be realized by statistical processing on pixel values of ridge line direction image data. The direction smoothing process is, for example, a process of taking a mode value of a direction component of a region within a certain range, or an average of direction vectors of a region within a certain range.

Figure 7:
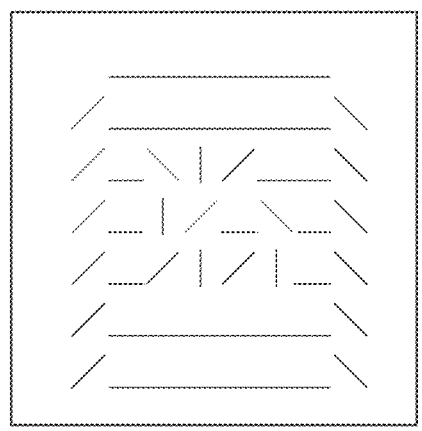
FIG. 7 is a diagram for describing a direction smoothing process performed inside the singular region detection unit according to the first exemplary embodiment, schematically showing ridge line direction image data before the direction smoothing process.
Figure 8:
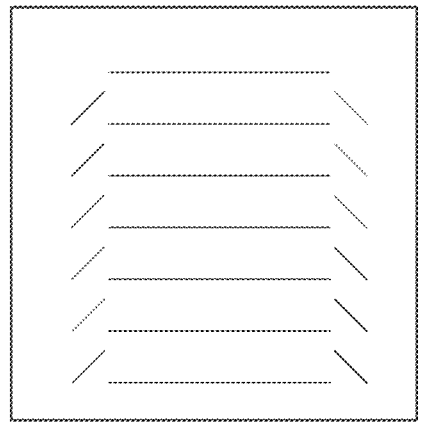
FIG. 8 is a diagram for describing a direction smoothing process performed inside the singular region detection unit according to the first exemplary embodiment, schematically showing ridge line direction image data after the direction smoothing process.

FIG. 7 and FIG. 8 are schematic diagrams for illustrating examples of the direction smoothing processing mentioned above. FIG. 7 shows for example ridge line direction image data obtained for the example for the fingerprint image in FIG. 6. In FIG. 6, the ridge line direction is indefinite with respect to the portion where the ridge line is broken. The ridge line direction image data for this type of portion is susceptible to noise. This is because the direction of the ridge line to be detected is not stable. Therefore, in the central portion in FIG. 7, the ridge line direction is not constant but random. FIG. 8 is an image obtained as a result of the direction smoothing process performed on the ridge line direction image in FIG. 7. By executing the direction smoothing process by means of the ridge line breakage detection unit 78 over a large area, it is possible to obtain a smoothly changing direction image shown in FIG. 8.

Then, the ridge line breakage detection unit 78 obtains an angular difference between the initial ridge line direction and the post-smoothing ridge line direction, for each portion in the direction image. When the angle (direction) has changed by a predetermined amount or more, that is, when the absolute value of the angular difference is equal to or larger than the predetermined amount, the ridge line breakage detection unit 78 extracts this portion as a ridge line breakage candidate region. Portions other than ridge line breakage marks due to burns or chemicals may be extracted as ridge line breakage candidate regions in some cases. For example, wrinkles and scars of elderly people or the like fall under this category. Such wrinkles and scars have thin line shapes, unlike burns and traces of chemicals. Therefore, the ridge line breakage detection unit 78 repeatedly performs image processing called expansion and contraction for the ridge line breakage candidate region extracted above, and removes such linear (or dot) fine traces.

Then, the ridge line breakage detection unit 78 finally calculates the total sum of the ridge line intensity already obtained by the above-described processing for this ridge line breakage candidate region, thereby calculating and outputting an evaluation value for the ridge line breakage detection. Then, when the evaluation value of the ridge line breakage output by the ridge line breakage detection unit 78 is equal to or greater than a predetermined threshold value, the singular region detection unit 61 determines the fingerprint as having a ridge line breakage trace therein. In other cases, the singular region detection unit 61 determines the fingerprint as being a fingerprint having no ridge line breakage trace.

That is to say, the singular region detection unit 61 acquires ridge line direction information for each portion included in the fingerprint image. In addition, the singular region detection unit 61 obtains smoothed ridge line direction information by performing direction smoothing processing based on ridge line direction information of a portion around each portion of the ridge line direction information. Furthermore, when (the absolute value of) the difference between the ridge line direction information and the smoothed ridge line direction information is greater than a predetermined threshold value, the singular region detection unit 61 detects a region corresponding to that portion as the singular region.

When it is determined as being a fingerprint having a ridge line breakage trace therein, the singular region detection unit 61 outputs the information on the position of the singular region.

Among ridge line breakages, there are not only the cases of burns and chemicals, but also cases of ridge line breakage due to years of aging deterioration and engaging in manual labor which abuses the hands. In the case of this type of natural breakage, not only a specific part but also the entire fingerprint ridge line is broken. In order to distinguish between this type of natural breakage of the entire ridge line and partial breakage (including intentional breakage) due to burns and chemicals, the singular region detection unit 61 may determine whether or not a portion of the fingerprint other than the ridge line breakage candidate region has a high-quality ridge line image. As a result, it becomes possible to detect only ridge line breakage due to a specific condition.

The singular region detection unit 61 may also determine whether or not a ridge line breakage trace is present in the central portion of the fingerprint. Since the fingerprint central portion has a significant influence on the determination of the fingerprint collation, ridge line breakage may be intentionally made in some cases. As a result, it also becomes possible to detect only ridge line breakage in a specific location.

((4) Cutout Work Detection)

The singular region detection unit 61 also has a function of detecting cutout work processing of the fingerprint. Specifically, the singular region detection unit 61 includes a cutout work detection unit 79. As will be described below, the cutout work detection unit 79 determines the presence or absence of cutout work processing with respect to the input fingerprint image, based on the change in the ridge line pitch (ridge line interval). This is because, in the case of a fingerprint with cutout work having been surgically done thereto, since the skin around the surgical operation mark is pulled while being sutured, the pitch of a specific portion of the ridge line and the pitch of the ridge line in a specific direction locally change.

Figure 9:
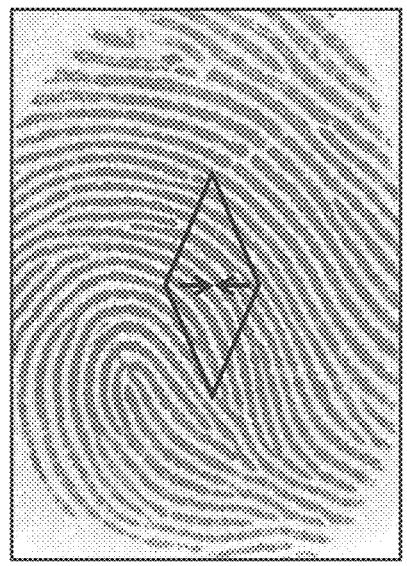
FIG. 9 is a schematic diagram for describing a cutting process of a fingerprint to be detected by the singular region detection unit according to the first exemplary embodiment, and is a diagram showing before the cutting process.
Figure 10:
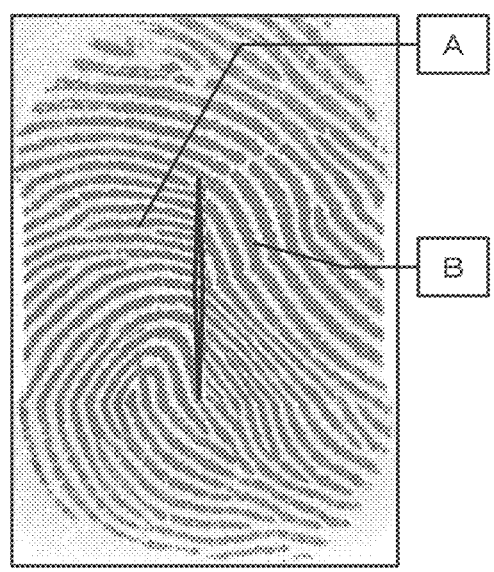
FIG. 10 is a schematic diagram for describing a cutting process of a fingerprint to be detected by the singular region detection unit according to the first exemplary embodiment, and is a diagram showing after the cutting process.

FIG. 9 and FIG. 10 are schematic diagrams for explaining the cutout work processing of fingerprints. FIG. 9 shows an example of a fingerprint image before the cutout work is performed. Further, FIG. 10 shows an example of a fingerprint image after the cutout work has been performed on the fingerprint shown in FIG. 9. An example of cutout work by surgery is a method such that a scalpel is placed in the diamond-shaped portion shown in the center of the fingerprint in FIG. 9, the epidermis is cut out thereinside, and while pulling the skin in the lateral direction, that is, in the left-right direction in a manner of closing the cut-out diamond shape, the center part of the original diamond shape is sutured.

In the case of performing a cutout work operation to achieve deformation on a fingerprint shown in FIG. 10, the ridge line, on the left hand side of FIG. 10, in the direction orthogonal to the cutout direction (that is, the ridge line running in the left-right direction in the present example. The portion indicated by "A" in FIG. 10) does not receive any change as a result of pulling. On the other hand, the ridge line, on the right hand side of FIG. 10, in the direction parallel to the cutout direction (that is, the ridge running in the vertical direction in this example. The portion indicated by "B" in FIG. 10) is observed with a characteristic in which the ridge line pitch spreads more than the original pitch.

A method of detection processing performed by the cutout work detection unit 79 is as follows.

The cutout work detection unit 79 first detects the scar position on which the cutout work has been performed. Specifically, a line segment of a certain length at an arbitrary angle from an arbitrary pixel in the image is generated, and the ridge line direction difference and the ridge line pitch difference are added for the image portion within a certain distance range (1 to 16 pixels) from line segments on both sides of the line segment. The coordinates (x, y) and angle (t) at which the sum value is a maximum are taken as a candidate for the scar position.

Next, the cutout work detection unit 79 calculates two types of cutout work evaluation values for rectangular regions (region R1 and region R2, respectively) of a predetermined size on both sides of the scar. The first evaluation value Wc1 is an index for checking whether or not the ridge line pitch in the same direction as the scar is widening. The second evaluation value Wc2 is an index for checking whether or not the ridge line pitches are different on both sides of the scar. The cutout work detection unit 79 calculates Wc1 and Wc2 by the following equations.

$$Wc1 = \max_{R=R1,R2} \left\{ \frac{(90 - \text{Angle difference between average direction within } R \text{ and } t)}{90} \times \right.$$
$$\left. \max\left(0, \frac{\text{Average pitch within } R - \text{Fingerprint average pitch}}{\text{Fingerprint average pitch}}\right) \times \right.$$

(Equation 3)

$$Wc2 = \frac{|\text{Average pitch within } R1 - \text{Average pitch within } R2|}{\text{Fingerprint average pitch}} \times \min\left\{\text{Average intensity within } R\right\} \quad \text{(Equation 4)}$$

(Average intensity within R1, Average intensity within R2)

That is to say, for each of the regions R1 and R2, when a product of a degree to which the ridge line direction in the region coincides with "t", a degree to which the ridge line pitch in the region is wider than the ridge line pitch of the entire fingerprint (0 when it is narrower than the ridge line pitch of the entire fingerprint), and the ridge line intensity in the region is obtained, the greater value is the evaluation value Wc1.

Further, the evaluation value Wc2 is the product of the degree of the difference between the ridge line pitches in the regions R1 and R2 and the ridge line intensity (the smaller one of the regions R1 and R2).

The average direction in the above equation is calculated by taking a weighted average with respect to the direction data generated by the ridge line direction detection unit 70 using weighting based on the ridge line intensity generated by the ridge line intensity detection unit 72. The average pitch in the above equation is calculated by taking a weighted average with respect to the pitch data generated by the ridge line pitch detection unit 71 using weighting based on the ridge line intensity generated by the ridge line intensity detection unit 72.

The determination by means of the evaluation values Wc1 and Wc2 calculated by the cutout work detection unit 79 is effective when the scar position is correctly detected. However, depending on the fingerprints, there are some cases where the position of the cutout work is unclear and the scar position cannot be clearly known. In order to cope with these types of cases, a method of detecting whether or not an unnatural broad pitch portion exists in the entire fingerprint is used concurrently, without using the scar position detected by the cutout work detection unit 79. Therefore, the following evaluation values Wc3 and Wc4 are used as indices. The evaluation value Wc3 is an index for seeing whether or not an abnormal wide pitch portion exists. The evaluation value Wc4 is an index for checking whether or not the pitch in a specific direction is widening. The cutout work detection unit 79 calculates Wc3 and Wc4 by the following equations.

$$Wc3 = \frac{\text{Total sum of ridge line intensities of 1.5 or more times fingerprint average pitch}}{\text{Total sum of ridge line intensities of entire fingerprint}} \quad \text{(Equation 5)}$$

$$Wc4 = \frac{\text{Average pitch of direction } Dm \times \text{average intensity of direction } Dm}{\text{Average pitch} \times \text{average intensity}} \quad \text{(Equation 6)}$$

In the equation of Wc4, Dm is a direction in which the average pitch is the maximum.

That is to say, the evaluation value Wc3 represents the ratio of the portion of the entire fingerprint where the ridge line pitch is wide (based on the pitch 1.5 times the average of the entire fingerprint), and is the value of the ratio with the ridge line intensities added.

The evaluation value Wc4 represents the ratio of the width of the pitch in the direction of a specific ridge line (the direction in which the average pitch is the maximum) of the entire fingerprint, and is the value of the ratio with the ridge line intensities added.

Finally, the cutout work detection unit 79 outputs the above-described four types of evaluation values Wc1, Wc2, Wc3, and Wc4. Then, the singular region detection unit 61 determines whether or not cutout work is included in the fingerprint image, depending on whether or not the respective values of the evaluation values Wc1, Wc2, Wc3, and Wc4 are equal to or greater than a predetermined threshold value. In addition, the singular region detection unit 61 multiplies each of these evaluation values Wc1, Wc2, Wc3, and Wc4 by a predetermined weight to obtain a weighted average (weighted average), and it is determined whether or not cutout work is included in the fingerprint image depending on whether or not the weighted average is equal to or greater than the predetermined threshold value.

That is to say, the singular region detection unit 61 acquires ridge line direction information as well as ridge line pitch information for each portion included in the fingerprint image. Moreover, the singular region detection unit 61 finds an evaluation value which takes a greater value as the difference in the ridge line direction and the difference in the ridge line pitch become greater between adjacent regions in the fingerprint image, based on the ridge line direction information and the ridge line pitch information. Further, when the evaluation value is greater than the predetermined threshold value, the singular region detection unit 61 detects that the adjacent region is a singular region due to cutout work.

When it is determined as being a fingerprint with cutout work done therein, the singular region detection unit 61 outputs the information on the position of the singular region.

Generally, in normal fingerprints, it is known that the pitch of the ridge line in the horizontal direction (short side direction of the finger) in the vicinity of the end of the lower part of the fingerprint tends to be wider than the ridge line pitch in the other portions. Based on this, in the processing described above, the region in the lower part of the fingerprint in which the ridge line is in the horizontal direction may be excluded from the calculation of the evaluation values Wc1, Wc2, Wc3, and Wc4. By performing the calculation of the evaluation values by the cutout work detection unit 79 in this manner, it is possible to further enhance the determination accuracy.

For example, when a person from whom a fingerprint is to be collected does not wish to authenticate themselves, the fingerprint is impressed while being intentionally twisted in some cases. Even in such a case, there is a tendency for the specific region of the fingerprint and the pitch in the specific direction to widen by pulling as a result of twisting. The evaluation values Wc3 and Wc4 that do not use the scar position can also be used for the purpose of detecting a fingerprint impressed in a state unsuitable for authentication where an action such as twisting is applied.

With the configuration of the first exemplary embodiment described above, the biological pattern information processing device 1 determines whether or not a singular region (a damaged portion or the like) exists in the acquired biological pattern, and if it exists, the position thereof can be specified.

Second Exemplary Embodiment

Next, a second exemplary embodiment will be described. Descriptions of matters common to those of the first exemplary embodiment may be omitted, and the following description focuses on matters unique to the second exemplary embodiment.

Figure 11:
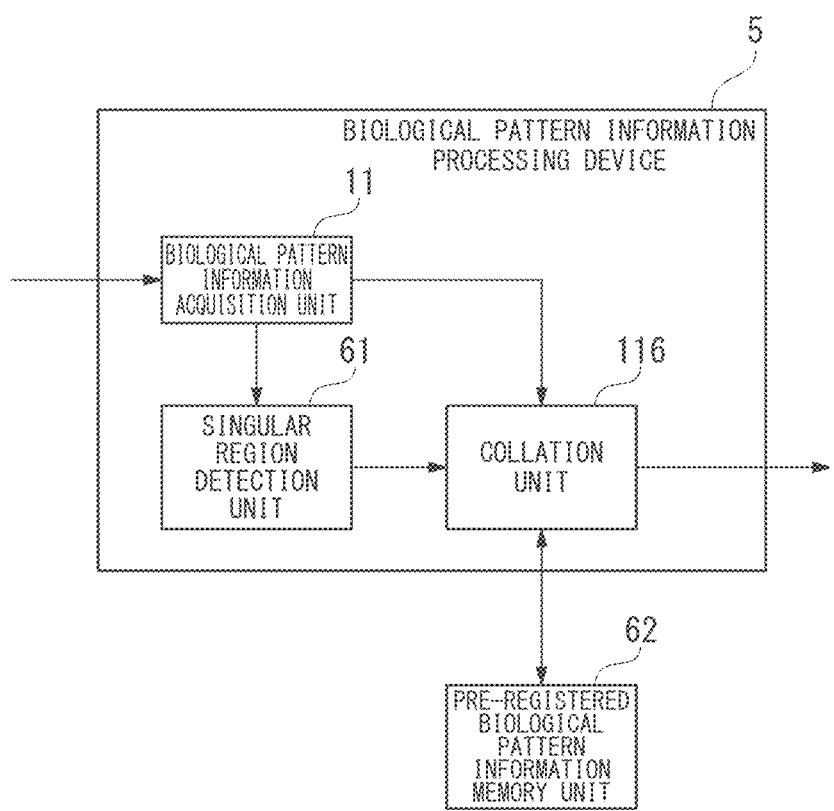
FIG. 11 is a block diagram showing a schematic functional configuration of a biological pattern information processing device according to a second exemplary embodiment.

FIG. 11 is a block diagram showing a schematic functional configuration of a biological pattern information processing device according to the second exemplary embodiment. As shown in FIG. 11, a biological pattern information processing device 5 according to the present exemplary embodiment includes an information acquisition unit 11, a singular region detection unit 61, and a collation unit 116.

In the present exemplary embodiment, a pre-registered biological pattern information memory unit 62 exists as an external function of the biological pattern information processing device 5. The function of the pre-registered biological pattern information memory unit 62 may be realized as a function of an independent device or may be realized as a function of a part of another device. In addition, the pre-registered biological pattern information memory unit 62 may be realized as a function inside the biological pattern information processing device 5.

The information acquisition unit 11 has a function similar to that in the first exemplary embodiment.

The singular region detection unit 61 has a function similar to that in the first exemplary embodiment.

The collation unit 116 performs processing of collating the biological pattern information in the region other than the singular region among the biological pattern information acquired by the information acquisition unit 11, with the pre-registered biological pattern information preliminarily registered in the pre-registered biological pattern information memory unit 62. The collation unit 116 acquires from the singular region 61 information on the presence or absence of a singular region and the position (range) of the singular region. The collation unit 116 is such that when performing the collation processing, at least either one of a positional deviation allowance which represents a degree to which positional deviation is allowed, and a mismatch allowance which represents a degree to which a mismatch is allowed may be variable. Further, when it is determined that there is a singular region based on the information output by the singular region detection unit 61, the collation unit 116 may perform adjustment so that either or both of the allowances change in a direction in which the allowance increases (that is to say, in a direction in which it is regarded that the degree of matching is increased despite some differences).

A fingerprint that is damaged due to a surgical operation or an injury maintains the characteristic amount of the original fingerprint except for the portion of the surgical operation or injury (that is, singular region). By verifying the consistency of this portion, there is a possibility that it can be collated with the fingerprint before the surgical operation or injury. For example, in characteristic point collation, whether or not the same fingerprint is present is determined by checking whether adjacent characteristic points (ridge line end points and/or branch points) of the fingerprint are at a certain distance difference or a certain angular difference. In the case of surgically operated fingerprints, in many cases, this allowance is exceeded by shape change due to pulling at the time of suturing.

Therefore, for a fingerprint judged to be a damaged fingerprint, by mitigating the positional deviation allowance or mismatching allowance of fingerprint characteristics at the time of collation from a standard value, it is possible to manufacture a device that is characterized by being capable of collating with the finger of the principal person before the damage was made thereto.

When mitigating collation allowance, there is a disadvantage that the risk of erroneously identifying a different person as the principal person increases. However, in the operational environment in which an operator or the like ultimately confirms whether he/she is the same person or not using a face photograph or the like other than the fingerprint, it is possible to reduce this type of risk of misidentifying another person.

The collation process itself performed by the collation unit 116 can be performed using existing techniques. The outline of the process of collating a fingerprint is as follows. For the collation processing, the collation unit 116 extracts characteristics of the input fingerprint image. The characteristics include the ridge line directions of the fingerprint, the statistical values relating to distribution of the direction of the fingerprint, the manner of connection of ridge lines, the number of directional singular points of the ridge line for each type, the mutual positional relationship of the directional singular points, the orientation of straight lines connecting a plurality of directional singular points, and the angle formed by these straight lines. Ridge line directional singular points are directional singular points such as a true circular core, a semicircular core, and a delta, which will be described later. The collation unit 116 determines whether or not the plurality of fingerprint images are the same by evaluating the above-described characteristics of the plurality of fingerprint images with the proximity and/or the distance in the characteristic space. In one example, the collation unit 116 compares the characteristics of the fingerprint image preliminarily registered in the database against the newly input fingerprint image, and determines whether or not both images match.

In this type of collation processing, the above-mentioned positional deviation allowance is for example a value that represents the degree to which the error in the position of the characteristic point in the fingerprint image is allowed. In addition, the mismatching allowance is a value that indicates the degree to which characteristic mismatching is still allowed while it is regarded as matching when the two fingerprint images to be compared do not completely match. For example, the mismatching allowance may be represented by a distance that is appropriately defined in the characteristic space, or may be expressed by the degree of the weight of the penalty that is given according to the distance.

The pre-registered biological pattern information memory unit 62 memorizes pre-registered biological pattern information. The pre-registered biological pattern information memory unit 62 holds the biological pattern information and the identification information for identifying the individual while associating them with each other. In addition, the pre-registered biological pattern information memory unit 62 may further hold the above identification information with personal attribute information while associating them with each other. An example of individual attribute information is the full name, the information on the registered residence, and the information on the legal status of the individual. The pre-registered biological pattern information memory unit 62 uses, for example, a magnetic hard disk device, a semiconductor memory, or the like as a means for storing information.

With the configuration of the second exemplary embodiment described above, the collation unit 116 can perform the collation processing using the biological pattern information of the region other than the detected singular region.

Further, when the singular region is detected, the collation unit 116 can mitigate the positional deviation and perform the collation process.

Moreover, when the singular region is detected, the collation unit 116 can mitigate the mismatching allowance and perform the collation process.

Third Exemplary Embodiment

Next, a third exemplary embodiment will be described. Descriptions of matters common to those of the above exemplary embodiment may be omitted, and the following description focuses on matters unique to the present exemplary embodiment.

Figure 12:
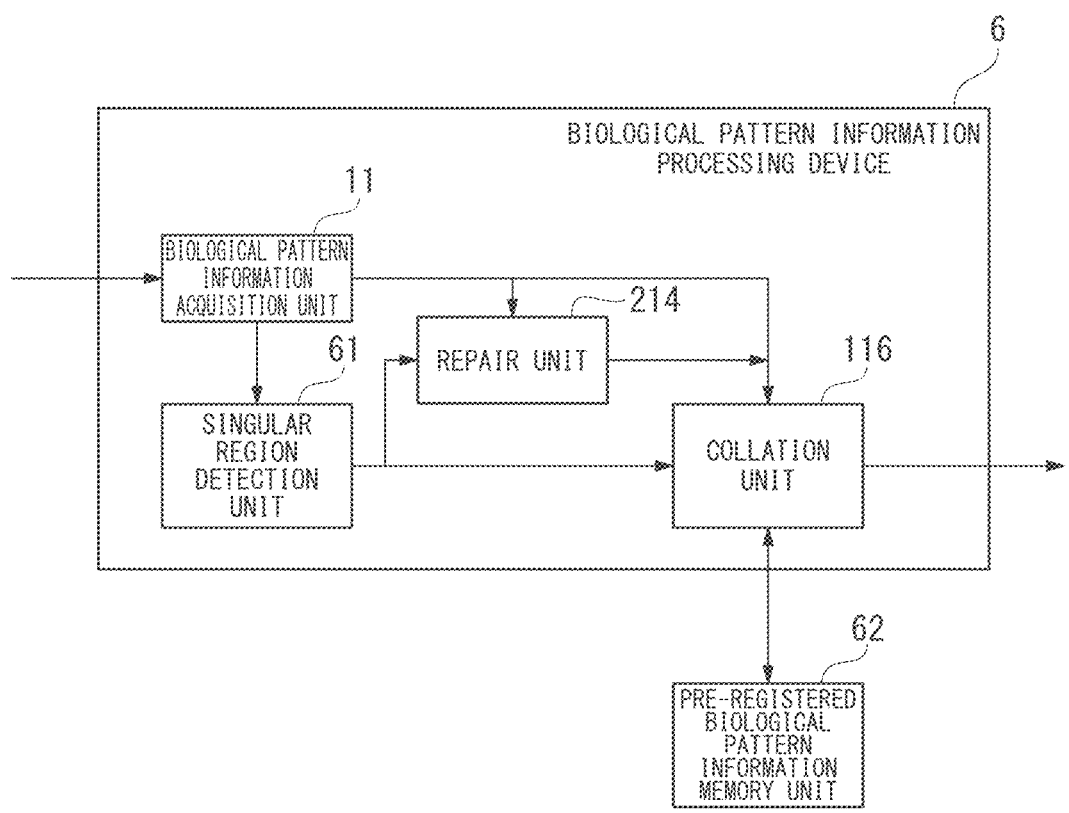
FIG. 12 is a block diagram showing a schematic functional configuration of a biological pattern information processing device according to a third exemplary embodiment.

FIG. 12 is a block diagram showing a schematic functional configuration of a biological pattern information processing device according to the third exemplary embodiment. As shown in FIG. 12, a biological pattern information processing device 6 according to the third exemplary embodiment includes an information acquisition unit 11, a singular region detection unit 61, a repair unit 214, and a collation unit 116.

Each of the information acquisition unit 11, the singular region detection unit 61, and the collation unit 116 has the same function as each function in the above-described exemplary embodiment. The biological pattern information processing device 6 according to the present exemplary embodiment is characterized in that it includes a repair unit 214.

The repair unit 214 repairs damage in the biological pattern information that has occurred in the singular region of the biological pattern information included in the singular region in the biological pattern information acquired by the information acquisition unit 11.

Then, in the present exemplary embodiment, the collation unit 116 regards the biological pattern information repaired by the repair unit 214 as a region other than the singular region, and performs a collation process.

Next, details of the process performed by the repair unit 214 will be described. The repair unit 214 performs the process of repairing a fingerprint of a singular region caused by a surgical operation called "Z type surgery". The Z type surgery is a surgical operation in which a scalpel is put into the fingerprint epidermis in a Z shape and the skins of the two triangular portions created as a result of the Z-shaped incision are replaced and then sutured again. When such surgery is performed, a positional change of the fingerprint characteristic amount occurs, so that it is difficult or impossible to collate it as it is with the fingerprint before the surgery.

Figure 13:
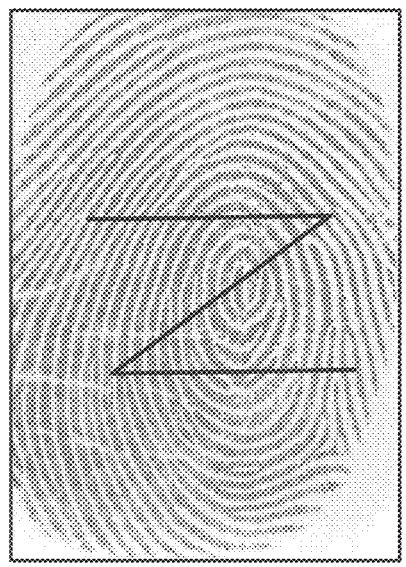
FIG. 13 is a schematic diagram for describing Z type surgery to be detected by the singular region detection unit according to the third exemplary embodiment, showing an example of a fingerprint image before performing the Z type surgery.
Figure 14:
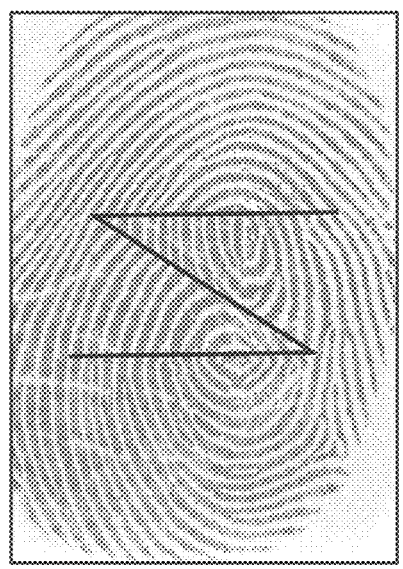
FIG. 14 is a schematic diagram for describing Z type surgery to be detected by the singular region detection unit according to the third exemplary embodiment, showing an example of a fingerprint image after performing the Z type surgery.

FIG. 13 and FIG. 14 are schematic diagrams showing examples of fingerprint images for explaining Z-type surgery. FIG. 13 shows an image before performing the Z type surgery. Further, FIG. 14 shows an image after performing the Z-type surgery. By replacing and suturing the two triangular skins created as a result of the Z-shaped incision described above, the fingerprint image shown in FIG. 14 has a pattern which is not normally possible.

The fingerprint image shown in FIG. 14 is an abnormal fingerprint. The repair unit 214 repairs the fingerprint image shown in FIG. 14 created as a result of the Z type surgery, that is to say, performs a process for processing the image, and performs a process for restoring it to the original fingerprint image (before the surgery) in FIG. 13.

Figure 15:
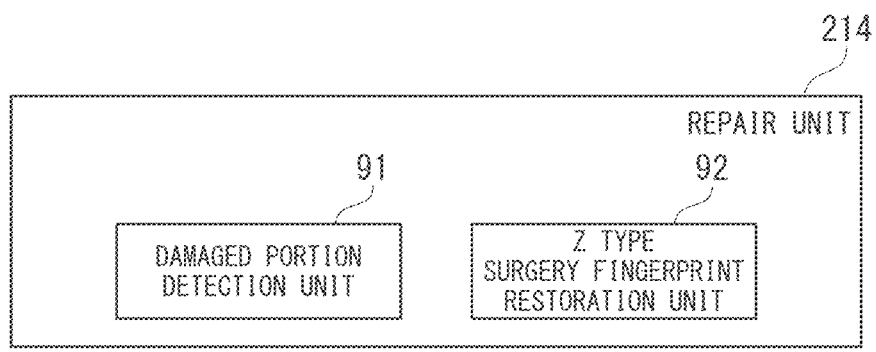
FIG. 15 is a block diagram showing a schematic functional configuration inside a repair unit according to the third exemplary embodiment.

FIG. 15 is a block diagram showing a schematic functional configuration inside the repair unit 214. As shown in FIG. 15, the repair unit 214 includes thereinside a damaged portion detection unit 91 and a Z type surgery fingerprint restoration unit 92, in an interior thereof.

Hereinafter, a method of processing performed by the repair unit 214 will be described.

The damaged portion detection unit 91 detects a portion of the trace on which the operation has been performed from the fingerprint image, and outputs an abnormality degree image representing the degree of abnormality as an image. As an example, in the abnormality degree image, the degree of abnormality is represented in grayscale in the image.

As the degree of abnormality, the damaged portion detection unit 91 uses any one of a comb type evaluation value $Wk(x, y)$, a $\omega$ type evaluation value $Wo(x, y)$, and an X type evaluation value $Wx(X, y)$ calculated by the singular region detection unit 61. The damaged portion detection unit 91 may receive these various evaluation values from the singular region detection unit 61, or the damaged portion detection unit 91 itself may calculate these various evaluation values by means of a similar method. In addition, the damaged portion detection unit 91 may use another evaluation value (for example, a value indicating the degree of direction change or pitch change as described above) as the degree of abnormality. The damaged portion detection unit 91 may use a weighted average value obtained by weighting these various evaluation values and taking the average as the abnormality degree. Then, the damaged portion detection unit 91 creates an abnormality degree image using one of the abnormality degrees described here.

The Z type surgery fingerprint restoration unit 92 receives input of two images of a fingerprint image and an abnormality level image created by the damaged portion detection unit 91, and outputs a processed fingerprint restored image.

Specifically, first, the Z type surgery fingerprint restoration unit 92 applies Hough transformation to the abnormality degree image. As a result of this Hough transformation, the Z type surgery fingerprint restoration unit 92 detects straight line components in the abnormality degree image. Then, the Z type surgery fingerprint restoration unit 92 detects three straight line components (from the first candidate up to the third candidate) in which the portions with high abnormality degrees (dark portions in the case where it is expressed as an abnormality degree grayscale image) are linearly arranged. When these three straight line components from the first candidate to the third candidate form a "Z" shape on the fingerprint, the Z type surgery fingerprint restoration unit 92 determines that the fingerprint has undergone the Z shape processing.

In order to determine whether or not the three straight line components from the first candidate to the third candidate form a "Z" shape, the Z type surgery fingerprint restoration unit 92 uses the following conditions (1) to (3). The condition for determining a "Z" shape is that all of the following conditions (1) to (3) are satisfied. A proviso is that in the condition (1) to the condition (3), the three straight line components that are the first candidate to the third candidate are represented by straight lines (line segments) A, B, and C.

Condition (1): Two straight lines A and B the orientation (angle) of which are closest to each other are near parallel. Specifically, the difference between the orientations of the straight line A and the straight line B is within 15 degrees, and also the straight lines A and B do not intersect within the image range.

Condition (2): A straight line C other than A and B intersects each of the straight lines A and B in the image range at a difference of orientation (angle) of not less than 20 degrees and not more than 60 degrees.

Condition (3): The average value of the pixel values of the abnormality degree images on the straight lines (line segments) A, B, and C is equal to or greater than a predetermined threshold value for each line segment (for all three lines).

Figure 16:
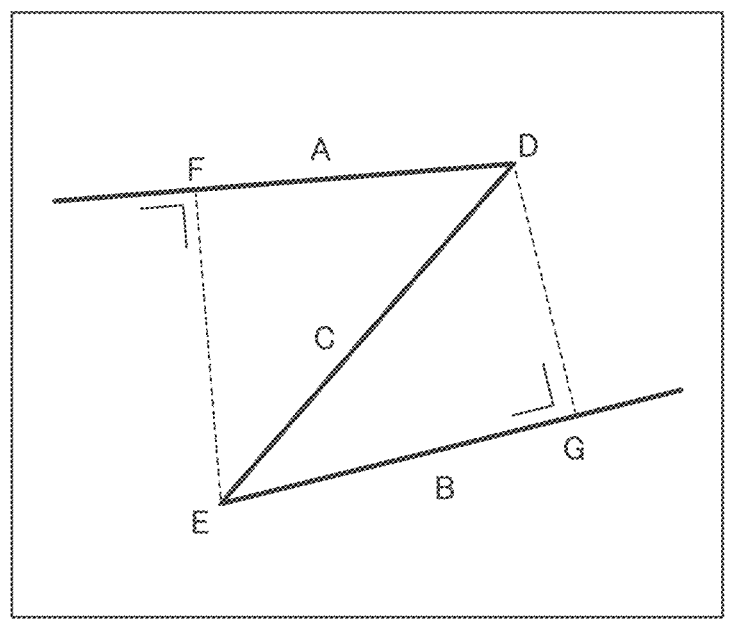
FIG. 16 is a schematic diagram showing a method of performing a restoration process based on an image of a Z type surgery fingerprint by means of the repair unit according to the third exemplary embodiment.

FIG. 16 is a schematic diagram for explaining the method of restoring a Z type surgery fingerprint. When it is determined that the input fingerprint image is a Z type surgery fingerprint, the Z type surgery fingerprint restoration unit 92 restores the preoperative image by the following method (Step (1) to Step (6)), and outputs the obtained preoperative image. FIG. 16 shows three straight line component candidates (straight lines A, B, C) in the abnormal value image detected at the time of the above determination. Moreover, FIG. 16 shows points D, E, F, and G used in the restoration procedure described below.

Step (1): The point of intersection between the straight line A and the straight line C is taken as D, and the intersection between the straight line C and the straight line B is taken as E.

Step (2): The foot of the perpendicular drawn from the intersection point E onto the straight line A (the intersection between the perpendicular line and the straight line A) is taken as F.

Step (3): The foot of the perpendicular drawn from the intersection point D onto the straight line B (the intersection between the perpendicular line and the straight line B) is taken as G.

Step (4): Copy the portion surrounded by the triangle FDE (first polygon) of the input image onto the triangle FGE of the output image by means of affine transformation.

Step (5): Copy the portion surrounded by the triangle DEG (second polygon) of the input image onto the triangle DFG of the output image by means of affine transformation.

Step (6): The regions other than the portions copied in the Steps (4) and (5) above are directly copied from the input image to the output image.

That is to say, based on the correlation between the ridge line direction information of each portion included in the fingerprint image and the template of the abnormal ridge line direction pattern held preliminarily, the repair unit 214 finds an evaluation value representing the degree of abnormal ridge line directional pattern possession in the ridge line direction information for each of the portions, and extracts the straight line component of the evaluation value in the fingerprint image. In addition, the repair unit 214 mutually replaces the fingerprint images included in the first polygon and the second polygon defined based on these straight line components (if the shape of the polygon to be replaced differs from the shape of the original polygon, the shape is appropriately adjusted by means of affine transformation or the like) to thereby repair the damage.

Although the points F and G used in the above method are not necessarily guaranteed to be completely identical with the cutout part in the actual surgical operation, the characteristic amounts of the fingerprint images on the two triangles FGE and DFG used in the above Steps (4) and (5) can be expected to approach the position of the fingerprint before the surgical operation. That is to say, the repairing process of the repair unit 214 increases the possibility of successful collation with the pre-registered biological pattern information in the collation unit 116.

Further, in the case of handling a surgical fingerprint with a portion that has been clearly processed, by performing image matching (ridge line matching) at the boundary between the line segment DF and the line segment DE of the transformed portion, the repair unit 214 may correct the coordinate position of the point F which is the starting point F of the processing. Similarly, by performing image matching at the boundary between the line segment EG and the line segment ED of the transformed portion, the coordinate position of the point G serving as the starting point of processing may be corrected.

(Modification 1 of Repair Unit)

The process of the repair unit 214 may be performed in a manner of the following modification.

Here is described a case where the input fingerprint image is determined as containing cutout work damage, based on the evaluation values Wc1 and Wc2 calculated by the above-described cutout work detection unit 79. In this case, the repair unit 214 detects a rectangular region having a wide pitch on the wide pitch side of the detected scar, calculates the product of the region width and the pitch change difference in the rectangle, and estimates that it is the width of the cutout portion. As a result, it is possible to restore the peripheral portion of the fingerprint outside the diamond shape by performing image transformation such that the diamond region at the center part of FIG. 10 is inserted as a blank portion into the detection rectangular region of the image in FIG. 11.

(Modification 2 of Repair Unit)

As a further modification of the repair unit 214, a repair unit 214a described below may be used. The repair unit 214a according to the present modification does not restore the fingerprint before surgery by means of transformation, but excludes the portion where the fingerprint has been processed, extracts only the portion that has not been processed, and outputs the extracted result as a restored image. That is to say, the repair unit 214a cuts out a portion which has not been processed by means of surgery or the like.

Figure 17:
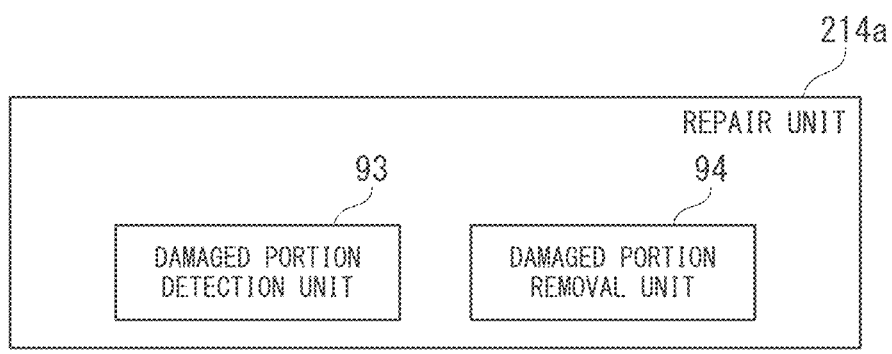
FIG. 17 is a block diagram showing a schematic functional configuration of a repair unit according to a modification of the third exemplary embodiment.

FIG. 17 is a block diagram showing a schematic functional configuration of the repair unit 214a according to present modification. As shown in FIG. 17, the repair unit 214a according to the present modification includes a damaged portion detection unit 93 and a damaged portion removal unit 94.

An example of the function of the damaged portion detection unit 93 is similar to the function of the damaged portion detection unit 91 described above. The damaged portion detection unit 93 may further include a function of detecting an abnormal wide pitch area or a function of detecting a ridge line damage region (a function similar to the above-described ridge line breakage detection unit 78). As a result, it is possible to detect a damaged portion while taking the information of the abnormality degree image into account.

Based on the abnormality degree image generated by the damaged portion detection unit 93, the damaged portion removal unit 94 decides an exclusion region to be excluded as a damaged portion by means of any of the methods listed below (method (1) to method (4)). Furthermore, the damaged portion removal unit 94 fills the exclusion region in the fingerprint image with a background color, and then outputs the image.

Method (1): A region whose degree of abnormality is equal to or greater than a predetermined threshold value and within 16 pixels in the vicinity thereof (this value "16" may be set to a different value) is taken as an exclusion region.

Method (2): Extracts a region where the degree of abnormality is equal to or greater than a predetermined threshold value, and treats the region including the region inside the abnormal region as an exclusion region by means of an image expansion/contraction process.

Method (3): A region where the degree of abnormality is equal to or greater than a predetermined threshold is taken as an abnormal region, and a fingerprint position that is furthest away from the abnormal region is detected. Also, a region within which the ridge line direction and the ridge line pitch continuously vary from that position (no abnormal discontinuity) within a predetermined distance is taken as an effective region. The portion other than the effective region is taken as an exclusion region.

Method (4): A region where the degree of abnormality is equal to or greater than a predetermined threshold is taken as an abnormal region, and a fingerprint position that is furthest away from the abnormal region is detected. Also, the region outside the circle which is a circle centered at that position and whose radius is the distance from that position to the abnormal region is taken as the exclusion region.

That is to say, the repair unit 214a repairs the damage by removing the information of the fingerprint image of the exclusion region determined based on the singular region, from the entire fingerprint image.

Whether to employ the method out of the above methods (1) to (4) can be controlled for example by parameters given from the outside. As another method, the method (4) is applied with the highest priority, and the method (3) is applied when the region (area) of the fingerprint image necessary for the collation processing cannot be obtained as a result thereof, and from thereon, the method (2) and the method (1) may be applied in this order in a similar manner.

Although the processing by the Z type surgery fingerprint restoration unit 92 supports only damaged fingerprints caused by surgery of a specific method, if there is no clear surgical trace, there is a possibility that the original preoperative fingerprint cannot be restored. Even in such a case, there is an advantage that it can still be collated with the fingerprint of the principal person before processing was done on the finger, by excluding the portion where the processing of the fingerprint has been performed, by means of the method using the damaged portion removal unit 94.

Also, the case of this modification, in terms of removing information on the damaged portion, is an example of a case where the repair unit 214a, concerning the biological pattern information included in a singular region among the biological pattern information acquired by the information acquisition unit 11, repairs the damage in the biological pattern information that has occurred in this singular region.

The process performed by the repair unit 214 (or a modification thereof) (the process of restoring a Z type surgery fingerprint to a state before surgical operation, or the process of excluding the damaged portion) does not necessarily guarantee accurate restoration of the fingerprint before the surgery. For example, a normal fingerprint of a finger without a surgery history may be determined as having undergone a surgical operation as a result of a false determination, and there may be some cases where it may still be processed. However, for example, by means of the collation unit 116 checking both the fingerprint image prior to the processing by the repair unit 214 (or a modification thereof) and the processed fingerprint image against the pre-registered biological pattern information memory unit 62 (fingerprint database), it is possible to reduce the risk of lowering the authentication rate. When collating both fingerprint images of before and after processing with the pre-registered biological pattern information memory unit 62, if one of the fingerprint images coincides with the pre-registered biological pattern, it can be regarded as matching with the pre-registered biological pattern.

Also, as a result of the processing performed by the repair unit 214 (or a modification thereof), there is also a risk that the fingerprint image after the restoration process coincides with the fingerprint of another person. However, if the operation is performed such that an operator or the like separately makes a confirmation using means other than fingerprints (for example, a face photograph, etc.) instead of making a final decision based only on that match, this type of risk in misidentification of another person can be reduced.

According to the configuration of the third exemplary embodiment described above, when the singular region is detected, the biological pattern information can be repaired. One method of restoration is to exclude the excluded region including the singular region from the collation process target. Another method of restoration is to restore the biological pattern replacement when a surgical operation or the like has been done, and perform the collation process based on the characteristics after restoration to the original has been done. As a result, accuracy in detecting a preliminarily registered specific biological pattern is improved.

The functions of the biological pattern information processing device in the above-described exemplary embodiments may be realized by a computer. In this case, it may be realized by recording a program for realizing the functions of this device on a computer-readable recording medium, and by causing the computer system to read and execute the program recorded on the recording medium. The term "computer system" referred to here includes hardware such as an OS and peripheral devices. Moreover, the term "computer-readable recording medium" refers to a portable medium such as a flexible disk, a magnetic optical disk, a ROM, and a CD-ROM, or a memory device such as a hard disk built in a computer system. Furthermore, the "computer-readable recording medium" may include one that dynamically holds a program for a short time, such as a communication line for transmitting a program via a network such as the Internet or a communication line such as a telephone line, and one that holds a program for a certain period of time such as a volatile memory inside a computer system serving as a server or a client in that case. Further, the program above may be for realizing a part of the above-described functions, or may be one which can realize the above-mentioned functions in combination with a program already recorded in the computer system.

The exemplary embodiments of the present invention have been described above in detail with reference to the figures. However, the specific configuration is not limited to these exemplary embodiments, and designs and the like not departing from the scope of the present invention are included.

INDUSTRIAL APPLICABILITY

The present invention can be applied to a social system that uses biological pattern collation.

REFERENCE SYMBOLS 1, 5, 6 Biological pattern information processing device
11 Biological pattern information acquisition unit
61 Singular region detection unit
62 Pre-registered biological pattern information memory unit
70 Ridge line direction detection unit
71 Ridge line pitch detection unit
72 Ridge line intensity detection unit
73 Direction singular point detection unit 74 Abnormal pattern detection unit
75 Comb type direction pattern detection unit
76 œ type direction pattern detection unit
77 X type direction pattern detection unit
78 Ridge line breakage detection unit
79 Cutout work detection unit
91, 93 Damaged portion detection unit
92 Z type surgery fingerprint restoration unit
94 Damaged portion removal unit
116 Collation unit
214, 214a Repair unit

The invention claimed is:

1. A fingerprint image information processing device comprising:
at least one memory storing instructions; and
at least one processor configured to execute the instructions to:
acquire image information indicating an image of a finger;
detect a directional singular point of a ridge line from the image; and
detect a singular region indicating damage of the finger, by determining whether a detection result of the directional singular point satisfies a condition of any of an arch-shaped pattern, a loop-shaped pattern, a spiral-shape pattern, and a variant-shaped pattern.

2. The fingerprint image information processing device according to claim 1,
wherein the at least one processor is configured to execute the instructions to:
acquire ridge line direction information corresponding to a portion included in the image;
find an evaluation value for each ridge line direction information, based on a correlation between each ridge line direction information, and a template of an abnormal ridge line direction that is preliminary held, the evaluation value indicating a degree of possession of an abnormal ridge line direction pattern; and
detect a portion corresponding to ridge line direction information for which the evaluation value is equal to or greater than a predetermined threshold value, as the singular region.

3. The fingerprint image information processing device according to claim 1,
wherein the at least one processor is configured to execute the instructions to:
acquire ridge line direction information corresponding to a portion included in the image;
obtain smoothed ridge line direction information by performing direction smoothing processing for each ridge line direction information, based on ridge line direction information corresponding to a region located around a region corresponding to the ridge line direction information; and
detect a region corresponding to the ridge line direction information in which a difference between the ridge line direction information and the smoothed ridge line direction information is greater than a predetermined threshold value, as the singular region.

4. The fingerprint image information processing device according to claim 1,
wherein the at least one processor is configured to execute the instructions to:
acquire ridge line direction information and ridge line pitch information corresponding to a region included in the image;
find an evaluation value based on the ridge line direction information and the ridge line pitch information, the evaluation value taking a greater value as a difference in ridge line directions and a difference in ridge line pitches become greater between adjacent regions in the image; and
in a case where the evaluation value is greater than a predetermined threshold value, detect that the adjacent regions are a singular region due to cutout work.

5. The fingerprint image information processing device according to claim 1,
wherein the at least one processor is configured to execute the instructions to:
collate image information corresponding to a region other than the detected singular region among the acquired image information, and image information registered in advance in association with identifying information for identifying an individual.

6. The fingerprint image information processing device according to claim 5, wherein the at least one processor is configured to execute the instructions to:
when performing the collation processing, make at least either one of a positional deviation allowance and a mismatch allowance variable, the positional deviation allowance representing a degree to which positional deviation is allowed, and the mismatch allowance representing a degree to which a mismatch is allowed.

7. The fingerprint image information processing device according to claim 5,
wherein the at least one processor is configured to execute the instructions to:
repair damage of the image information corresponding to the singular region in the obtained image information; and
regard a region corresponding to the repaired image information as the region other than the singular region, and perform the collation.

8. The fingerprint image information processing device according to claim 7, wherein the at least one processor is configured to execute the instructions to:
exclude an exclusion region defined based on, the singular region, from the image, to thereby repair the damage.

9. The fingerprint image information processing device according to claim 7,
wherein the at least one processor is configured to execute the instructions to:
find an evaluation value for each portion included in the image, based on a correlation between ridge line direction information and a template of an abnormal ridge line direction pattern that is preliminary held, the evaluation value representing a degree to which the ridge line direction information has an abnormal ridge line directional pattern;
extract a straight line component of the evaluation value in the image; and
repair the damage by mutually replacing images included in a first polygon and a second polygon defined based on the extracted straight line components.

10. A fingerprint image information processing method executed by a computer, the method comprising:
acquiring image information indicating an image of a finger;
detecting a directional singular point of a ridge line from the image; and
detecting a singular region indicating damage of the finger, by determining whether a detection result of the directional singular point satisfies a condition of any of an arch-shaped pattern, a loop-shaped pattern, a spiral-shaped pattern, and a variant-shaped pattern.

11. A non-transitory computer-readable recording medium storing a computer-executable program, the program comprising:
- instructions for acquiring image information indicating an image of a finger;
- instructions for detecting a directional singular point of a ridge line from the image; and
- instructions for detecting a singular region indicating damage of the finger, by determining whether a detection result of the directional singular point satisfies a condition of any of an arch-shaped pattern, a loop-shaped pattern, a spiral-shaped pattern, and a variant-shaped pattern.

* * * * *